United States Patent [19]

Judd et al.

[11] Patent Number: 5,136,019
[45] Date of Patent: Aug. 4, 1992

[54] SYNTHETIC PEPTIDES FOR DIAGNOSIS AND PREVENTION OF INFLUENZA VIRUS INFECTION AND THEIR USE

[75] Inventors: Amrit K. Judd, Belmont, Calif.; Doris J. Bucher, New York, N.Y.

[73] Assignee: SRI International, Menlo Park, Calif.

[21] Appl. No.: 356,981

[22] Filed: May 24, 1989

[51] Int. Cl.$^5$ .................. C07K 7/00; A61K 37/00
[52] U.S. Cl. ................... 530/326; 530/324; 530/389.4; 530/391.34; 514/13
[58] Field of Search ............. 530/324, 326; 514/13

[56] References Cited

U.S. PATENT DOCUMENTS

| | | | |
|---|---|---|---|
| 4,588,680 | 5/1986 | Bucher et al. | 435/5 |
| 4,597,967 | 7/1986 | Beachey | 424/88 |
| 4,625,015 | 11/1986 | Green et al. | 530/324 |
| 4,713,366 | 12/1987 | Stevens | 514/13 |
| 4,981,782 | 1/1991 | Judd et al. | 435/5 |

FOREIGN PATENT DOCUMENTS

8403564 9/1984 PCT Int'l Appl. .

OTHER PUBLICATIONS

Niman, H. L. et al. (1983), *Proc. Natl Acad Sci* (USA), 80, 4949–4953.
Sutcliffe, J. G. et al. (1983) *Science*, 219, 660–666.
Hopp, T. P. et al. (1983) *Proc. Natl. Acad. Sci* (USA), 78, 3824–3828.
Heath, R. L. (1980) CRC Handbook of Chemistry and Physics 60th Ed., pp. B236–B320.
Webster et al., (1977), *Infection and Immunity* 17(3):561–566.
Kahn et al., (1982) *J. Clinical Microbiology*, 16(5):813–820.
Van Wyke et al., (1984) *J. Virol.* 49(1):248–252.
McQuillin et al., (1985) *Lancet* 2:911–914.
Ye et al., (1987) *J. Virol.* 61(2):239–246.
Joassin et al., (1987) *Arch. Virol.* 95:183–195.
Gotch et al., (1987) *Nature* 326:881–882.
Bucher et al., (1987) *J. Immunol. Methods* 96:77–85.
Judd et al., Derwent Abstract of U.S. Ser. No. 050,633 and foreign equivalents.
Sigma Chemical Co., brochure, (Feb. 1982).
Weir, D. M., *Handbook of Experimental Immunology* (1978) 1:15.1, 14.1–5, 18–37; 3:40.2–3, A3.10–17.
Oxford et al., (1977) *Chemical Abstracts* 86(3):296.
Petrov et al., (1986) *Chemical Abstracts* 104(17):510.
Van Wyke et al., (1984) *Chemical Abstracts* 101(13):476.
Müller et al., (1982) *Proc. Natl. Acad. Sci.* 79(2):569–573.
Donofrio et al., (1986) *Chemical Abstracts* 105(5):548.

*Primary Examiner*—David M. Naff
*Assistant Examiner*—Jon P. Weber
*Attorney, Agent, or Firm*—Richard P. Lange

[57] ABSTRACT

Synthetic polypeptides having influenza virus antigenic properties are disclosed. These polypeptides correspond substantially to the 215 to 235 region of the matrix protein of influenza virus. Salts, derivatives, and conjugates of these polypeptides are disclosed as well as methods for using these materials for diagnostic and medical/veterinary purposes.

6 Claims, No Drawings

SYNTHETIC PEPTIDES FOR DIAGNOSIS AND PREVENTION OF INFLUENZA VIRUS INFECTION AND THEIR USE

The invention described herein was made in the course of work under a contract from the United States Department of Defense (DAMD-17-85-C-5019 United States Army).

BACKGROUND OF THE INVENTION

Reference to Related Application

U.S. patent application Ser. No. 050,633, filed May 14, 1987 is related to this application. It concerns synthetic peptides corresponding to the 79-104, 64-80 and 149-169 regions of M-protein and their use in the diagnosis and treatment of influenza.

Field of the Invention

The present invention relates to antigens for influenza. More particularly, it relates to synthetic peptide sequences which present influenza antigenic determinants, the use of these sequences as antigens in the preparation of diagnostic reagents and vaccines, the formation of antibodies, and the like and the use of these peptides, reagents, antibodies and vaccines in the diagnosis, prevention and treatment of influenza virus infections.

Background Materials

The Importance of Influenza

Influenza remains an important infection which can cause epidemics or pandemics following emergence of new strains. A network of surveillance laboratories has been set up worldwide, but despite these efforts influenza is still considerably under-reported. This is at least in part due to the lack of rapid and reliable tests for use in laboratories that are only moderately well equipped. In addition, effective drugs such as amantadine are underutilized for treatment or prophylaxis, particularly in the elderly, because rapid methods of diagnosis are not commonly available.

The problem is further complicated by the tendency of the responsible virus to continually reappear as different strains. It has been shown that as these new strains emerge they present "drift" or "shift" of their surface antigenic determinants that can make their immunologic identification problematic when based on these determinants. It has been shown that the structure of the matrix protein of the influenza virus is highly conserved from strain to strain.

The Matrix Protein

The matrix protein (or "M protein") of influenza is the major internal protein of the influenza virion. It is known to comprise as much as 46% of the total viral protein, to have a molecular weight of about 27,000 and to line the inner surface of the lipid bilayer of the envelope that contains the virus' hemagglutinin and neuraminidase subunits. Its peptide chain contains 252 amino acids. Its amino acid sequence has been reported.

A number of workers have examined various aspects of the matrix protein's role in connection with influenza. Webster and Hinshaw in *Infection and Immunity* (Sept 1977) 17,(3):561-566 reported that intact isolated M protein enhanced virus clearance in mice. Coinventor Bucher and her coworkers, in *J. Clin. Microbiol.* (November 1982) 16,(5):813-820 used intact isolated M protein in an enzyme-linked immunosorbent assay (ELISA) to detect antibodies to influenza virus. Zvonarjev and Ghendon in *J. Virol.* (February 1980) 33(2):583-586, reported that transcriptase activity of influenza A virus ribonucleoproteins was inhibited in the presence of M protein. Ye, Z., R. Pal, J. W. Fox, and R. R. Wagner. (1987) in "Functional and antigenic domains of the matrix (M) protein of influenza A virus" *J. Virol.* 61: 239-246; reported that the monoclonal antibodies reverse the inhibited transcription.

In an earlier patent application, the synthesis and use of synthetic polypeptides corresponding to the 79-104, 64-80 and 149-169 regions of M-proteins were described.

Other references relating to the properties of the M protein include the report of coinventor Bucher and her coworkers which showed that purified intact M protein can elicit an antibody response in rabbits at a titer of 1:40,000 *J. Immunol. Methods* (1987) 96:77-85; the report of Van Wyke et al in *J. Virol.* (1984) 48:248-252 of multiple antigenic domains in the M protein structure; and McQuillin et al's work, reported in *Lancet* (Oct. 26, 1985) 2,(8461):911-914, on monoclonal antibodies to influenza M protein and their use in influenza diagnosis. See also: Allen, H., J. McCauley, M. Waterfield, and M. J. Gething. (1980) "Influenza virus RNA segment 7 has the coding capacity for two polypeptides" Virology 107:548-551; Baylor, N. W., Y. Li, Z. Ye, and R. R. Wagner. (1988) "Transient expression and sequence of the Matrix (M1) gene of WSN influenza A virus in a vaccinia vector" *Virol.* 163:618-621; Markushin, S., H. Ghiasi, N. Sokolov, A. Shilov, B. Sinitsin, D. Brown, A. Klimov, and D. Nayak. (1988) "Nucleotide sequence of RNA segment 7 and the predicted amino sequence of M1 and M2 proteins of FPV/Weybridge (H7N7) and WSN (H1N1) influenza viruses" *Virus Research* 10:263-272; Ortin, J., C. Martinez, L. Mercedes Davila, C. Lopez-Galindez, N. Villanueva, and E. Domingo. (1983) "Evolution of the nucleotide sequence of influenza virus RNA segment 7 during drift of the H3N2 subtype" *Gene* 23:233-239; and Zvonarjev, A. Y. and Y. Z. Ghendon. (1980) "Influence of membrane (M) protein on influenza A virus virion transcriptase activity in vitro and its susceptibility to rimantadine" *J. Virol.* 33:583-586.

Other Work

Other work related to the general subject of influenza and its diagnosis and treatment includes Grandien, et al., who reported in *J. Clin. Microbiol.* (November 1985) 22(5):757-760 their studies comparing two immunoassay techniques for diagnosis of influenza infections; and Shalit, et al., who reported in *J. Clin. Microbiol.* (November 1985) 22,(5):877-879 their studies comparing monoclonal antibodies and polyclonal antisera for diagnosis of influenza infections.

Other references relating to the general subject of diagnosis of influenza infection include, for example, Julkumen, I, et al. (1984) *J. Virol. Methods* 9(1):7-14; Zhurov, S. A., et al. (1985) *Za. Microbiol. Epidemiol. Immunobiol.* (1):81-5 (Eng. Abstr.); Ptakova, M., et al. (1985) *Acta Virol.* (Praha) 29(1):19-24; Bukrinskaia, A. G. (1985) *Vopro. Viromol.* 30(1):16-21 (61 ref.); Anestad, G. (1985) *J. Hyg.* (London) 94(3):349-56; Kobiakova, T. N. (1985) *Microbiol. Epidemiol. Immunobiol.* (4):43-5; Van Voris, L. P., et al. (1985) *J. Med. Virol.*

16(4)315-20; and (1984) *Vopro. Viromol.* 29(4):417-9; Bucher et al. (1987) *J. Immunol. Methods* 96: 77-85.

Yet additional references of general interest to this invention include: Baez, M., P. Palese, and E. D. Kilbourne. (1980) "Gene composition of high-yielding influenza vaccine strains obtained by recombination" *J. Inf Dis.* 141:362-365; Bucher, D. J., I. G. Kharitonenkov, J. A. Zakormirdin, V. B. Gregoriev, S. M. Klimenko and J. F. Davis. (1980) "Incorporation of influenza virus M-protein into liposomes" *J. Virol.* 36:586-590; Bucher, D. J., S. S. L. Li, J. M. Kehoe, and E. D. Kilbourne. (1976) "Chromatographic isolation of the hemagglutinin polypeptides from influenza virus vaccine and determination of their amino terminal sequences" *Proc. Natl. Acad. Sci. USA,* 73:238-242; Buckler-White, A. J., C. W. Naeve, and B. R. Murphy. (1986) "Characterization of a gene coding for M-proteins which is involved in host range restriction of an avian influenza A virus in monkeys" *J. Virol.* 57:697-700; Chou, P. Y., and G. D. Fasman. (1978) "Empirical predictions of protein conformation" *Ann. Rev. Biochem.* 47:251-276; ElKaradaghi, S., J. A. Zakomirdin, C. Shimane, D. J. Bucher, V. A. Tverdislov, and I. G. Kharitonenkov. (1984) "Interaction of influenza virus proteins with planar bilayer lipid membranes. Characterization of their absorption and incorporation into lipid bilayers" *Biochem. Biophys. Acta.* 778:269-275; Erickson, B. W., and R. B. Merrifield. (1976) In: *The Proteins,* Vol. II. H. Neurath (ed), Academic Press, New York, 255-527; Fagraeus, A., and R. Norberg. (1987) "Anti-actin antibodies" *Curr. Topics Microbiol. Immunol.* 82:1-3; Gallagher, M., D. J. Bucher, R. Dourmashkin, J. F. Davis, G. Rosenn, and E. D. Kilbourne. (1984) "Isolation of immunogenic neuraminidases of human influenza viruses by a combination of genetic and biochemical procedures" *J. Clin. Microbiol.* 20:89-93; Gregoriades, A. (1977) "Influenza virus-induced proteins in nuclei and cytoplasm of infected cells" *Virology* 79:449-454; Guiffre, R. M., D. R. Tovell, C. M. Kay, and D. L. J. Tyrrell. (1982) "Evidence for an interaction between the membrane protein of a paramyxovirus and actin" *J. Virol.* 42:963-968; Gotch, F., J. Rothbard, K. Howland, and A. McMichael. (1987) "Cytotoxic T lymphocytes recognize a fragment of influenza virus matrix protein in association with HLA-2" *Nature* 326:881-882; Gregoriades, A. (1980) "Interaction of influenza M protein with viral lipid and phosphatidylcholine vesicles" *J. Virol.* 36:470-479; Hay, A. J., and J. J. Skehel. (1975) "Studies on the synthesis of influenza virus proteins" in *Negative Strand Viruses,* Ed. B. W. J. Mahy and R. D. Barry, vol. 2, pp. 635-655. Academic Press, New York and London; Kato, A., K. Mizumoto, and A. Ishihama. (1985) "Purification and enzymatic properties of an RNA polymerase—RNA complex from influenza virus" *Virus Research* 3:115-127; Khan, M. W., D. J. Bucher, A. K. Koul, G. Kalish, and E. D. Kilbourne. (1982) "Detection of antibodies to influenza virus M-protein through enzyme-linked immunosorbent assay (ELISA)" *J. Clin. Microbiology,* 16:813-820; Kilbourne, E. D. (1978) "Genetic dimorphism in influenza viruses: characterization of stably associated hemagglutinin mutants differing in antigenicity and biological properties" *Proc. Natl. Acad. Sci. USA* 75:6258-6262; Kyte, J., and R. F. Doolittle. (1982) "A simple method for displaying the hydropathic character of a protein" *J. Mol. Biol.* 157:105-132; Lamb, R. A. and C. J. Lai. (1981) "Conservation of the influenza virus membrane protein (M1) amino acid sequence and an open reading frame of RNA segment 7 encoding a second protein (M2) in H1N1 and H3N2 strains" *Virology* 112:746-751; Lowry, O. H., N. J. Rosebrough, A. L. Farr, and R. J. Randall. (1951) "Protein measurement with the Folin phenol reagent" *J. Biol. Chem.* 193:265-275; Maeno, K., S. Yoshii, T. Toshida, M. Iinuma, Y. Kawamoto, and T. Matsumoto. (1977) "Intracellular development of membrane protein of influenza virus" *Microbiol. Immunol.* 21:427-438; Novikoff, A. G., and E. Holtzman. (1976) *Cells and Organelles,* pp. 73-83, Holt, Rinehart and Winston, New York; Oxford, J. S., and G. C. Schild. (1975) "Immunological studies with influenza matrix protein" in *Negative Strand Viruses,* Ed. B. W. J. Mahy and R. D. Barry, vol. 2, pp. 611-620. Academic Press, New York and London; Panicali, D., and E. Paoletti. (1982) "Construction of poxviruses as cloning vectors: Insertion of the thymidine kinase gene from herpes simplex virus into the DNA of infectious vaccinia virus" *Proc. Natl Acad. Sci. USA* 79:4927-4931; Patterson, S., J. Gross, and J. S. Oxford. (1988) "The intracellular distribution of influenza virus matrix protein and nucleoprotein in infected cells and their relationship to hemagglutinin in the plasma membrane" *J. Gen. Virol.* 69:1859-1872; Peeples, M. E. (1988) "Differential detergent treatment allows immunofluorescent localization of the Newcastle Disease virus matrix protein within the nucleus of infected cell" *Virol.* 162:255-259; Perkus. M. E., D. Panicali, S. Mercer, and E. Paoletti. (1986) "Insertion and deletion mutants of vaccinia virus" *Virology* 152:285-97; Perkus, M. E., A. Piccini, B. R. Lipinshas, and E. Paoletti. (1985) "Recombinant vaccine virus: Immunization against multiple pathogens" *Science* 229:981-984; Rothbard, J. B., R. Fernandez, and G. Schoolnik. (1984) "Strain-specific and common epitopes of gonococcal pili" *J. Exp. Med.* 160:208-221; Schmidtt, J. F. C., and H. G. Stunnenberg. (1988) "Sequence and transcriptional analysis of the vaccinia virus HindIII I fragment" *J. Virol.* 62:1889-1897; Schulze, I. T. (1970) "The structure of influenza virus. I. The polypeptides of the virion" *Virology* 42:890-904; Slabaugh, M., N. Roseman, R. Davis, and S. Mathews. (1988) "Vaccinia virus-encoded ribonucleotide reductase: sequence conservation of the gene for the small subunit and its amplification in hydroxyurea-resistant mutants" *J. Virol.* 62:519-527; Smith, G. L., J. Z. Levin, P. Palese, and B. Moss. (1978) "Synthesis and cellular location of ten influenza polypeptides individually expressed by recombinant vaccinia viruses" *Virology* 160:336-345; Tovell, D. R., J. S. Huang, I. A. McRobbie, G. A. Lund, and D. L. J. Tyrrell. (1984) "Potentiation of anti-actin antibody production by paramyxovirus M protein" p. 175, *Abstr. Sixth Int. Congress of Virol.* Sendai, Japan; Wakefield, L., and G. G. Brownlee. (1988) "RNA-binding activity of the influenza virus matrix protein" *Virus Res.* (VIREDF Supplement 2), p. 35; Voller, A., D. E. Bidwell, and A. Bartlett. (1976) "Enzyme immunoassays in diagnostic medicine. Theory and practice" *Bull. W. H.0.* 53:55-65; Winter, G., and S. Fields. (1980) "Cloning of influenza cDNA into M13: The sequence of the RNA segment encoding the A/PR/8/34 matrix protein" *Nucleic Acids Res.* 8:1965-1974.

These prior studies have been valuable to a general understanding of the influenza virus but have pointed up certain shortcomings. In particular, the use of purified materials such as purified M protein has the problem of contamination and batch-to-batch variation. Heterogeneity of the preparations used for assay is likely to give nonspecificity reactivities and false positiveness. Monoclonal antibodies, while theoretically attractive, can be of low avidity and low binding constant and thus of low value.

The only effective antiviral drug for influenza virus is amantadine or its close relative rimantadine. Although these drugs can be quite effective against influenza, they are only effective against diseases caused by type A influenza virus. These drugs are not well tolerated in the most needy group of individuals at highest risk for morbidity and mortality—the elderly. In individuals with poor renal clearance, the drugs may accumulate producing convulsions; other central nervous system effects are lightheadedness, dizziness and problems of concentration. In addition, the drug works most effectively as a prophylactic agent, therefore, one risks side effects in the absence of actual infection with influenza. Furthermore, the agent is only effective against type A influenza; considerable morbidity and mortality also occurs with type B influenza. An antiviral agent which would target the transcriptase would be specific for influenza virus and also free of the antigenic shift and drift associated with the surface antigens of influenza virus.

STATEMENT OF THE INVENTION

It has now been found that there are other synthetic polypeptides beyond those previously discovered which can react with preformed antibody to influenza A M protein, can stimulate influenza A M protein antibody response, can potentially serve as replacements for the native M protein in the selective diagnosis of infection with a wide range of strains of influenza virus and is recognized by monclonal antibodies to influenza A M protein. This antigenic reactivity of these proteins offers the potential that they can also be used as vaccinating agents to generate antibodies useful for prevention and/or treatment of a wide range of influenza A infections. These polypeptides can also be used as antiviral agents against influenza virus.

In particular, it has been found according to the present invention that synthetic polypeptides having from 5 to 25 and especially from 15 to 25 amino acid residues substantially corresponding to 15 to 25 amino acid residues in the 215 through 239 region of type A influenza M protein, have high influenza antigenic reactivity and are recognized by monoclonal antibodies. Conjugates of these peptides exhibit even greater influenza antigenic activity.

In other aspects, the invention concerns the salts of these polypeptides, the amide and acyl derivatives of the carbonyl and amino end groups of these polypeptides and their salts, and conjugates of these polypeptides with macromolecular carriers.

In an additional aspect, the invention concerns labeled versions of these polypeptides, their corresponding salts, derivatives and conjugates and their application to label-dependent assay methods such as radioimmunoassays (RIA) and enzyme-linked immunosorbent assays (ELISA).

In another aspect, this invention concerns methods of detecting the presence of influenza virus or diagnosing a state of influenza infection in an avian species or a mammalian species, particularly a human being, which methods are based on these synthetic polypeptides. In one of these methods, a sample taken from the subject is contacted under immunologic reaction conditions with a peptide of this invention, its salt, or its conjugate, optionally suitably labeled. If the subject was infected with influenza, the subject's sample will also contain antibodies to the influenza virus. The present peptides (or salts or conjugates) will react immunologically with a broad range of such antibodies. The occurrence or nonoccurrence of this immunologic reaction can be followed with conventional reporting mechanisms such as the ELISA or EMIT methods, radiolabels, fluorolabels or the like.

In a second representative example of these methods, the peptide or its salt or conjugate, optionally suitably labeled, competes with antigen in the sample for a quantity of added antibody with the results being based on the relative reaction of the competing antigen and peptide.

In another aspect, this invention relates to antibodies to these synthetic peptides or their salts or conjugates. These antibodies may be developed using a polypeptide (or a pharmaceutically acceptable salt thereof, or a conjugate of the peptide or a pharmaceutically acceptable salt thereof) as an immunogen to develop antibodies in a suitable host animal. Such antibodies may be used as diagnostic reagents in antibody-based assays such as the ELISA or EMIT assays or radioimmunoassay (RIA) techniques. The pure synthetic polypeptides, conjugates thereof, or antibodies prepared following this technique may also serve as calibration reagents in the ELISA, or EMIT, techniques as well as in other immunological assay techniques.

In another aspect, this invention concerns a method for immunization against influenza in a mammalian or avian species, particularly a human being, wherein the method comprises administering to the subject in need of such treatment a therapeutically effective amount of one or more or the synthetic polypeptides of the invention or a pharmaceutically acceptable salt or conjugate thereof or a vaccine produced therefrom, optionally in a pharmaceutically suitable adjuvant, carrier or diluent.

In another aspect, this invention concerns the use of the antibodies against these synthetic polypeptides or their conjugates or salts in methods of treatment of influenza. In such processes, the antibodies may serve as therapeutic agents by "passive immunization", a technique wherein partially purified immune sera from host animals or from hybridoma cell lines is to be injected into the influenza patient and has a therapeutic effect by binding to and neutralizing the infecting influenza virus.

As yet another aspect, this invention also concerns the use of the peptide or a pharmaceutically acceptable salt thereof, to inhibit the activity of polymerase of influenza virus as well as to inhibit transcriptase activity in influenza virus.

DETAILED DESCRIPTION OF THE INVENTION

Definitions

In the specification and claims, reference will be made to certain terms which are defined as follows.

As used herein:

"Acyl" refers to an alkyl-containing carbonyl group, e.g., R—C(=O)—, wherein R is an alkyl group having from 1 to 8 carbon atoms, such as methyl, ethyl, n-propyl, isopropyl, hexyl, octyl and the like. The acyl group usually preferred in this invention is acetyl. Acyl groups are used to block the terminal amino group of a polypeptide.

"Antibody" refers to a member of a family of glycosylated proteins called immunoglobulins, which can specifically combine with an antigen such as influenza antigen.

"Antigen" refers to a protein or peptide compound which will give rise to antibody formation.

"Antigenic determinant" or "antigenic determinant site" refers to the actual site of antibody recognition of the antigen. The term is used interchangeably with "epitope".

"Carrier" refers to a high molecular weight (macromolecular) polymeric material, usually a protein, to which an antigen or hapten can be bound or conjugated so as to facilitate antibody formation. Carriers can incorporate labels in their structure, if desired.

"Conjugate" refers to an antigen or hapten chemically bonded to a carrier; a conjugate can contain other groups, as well.

"ELISA" refers to an enzyme-linked immunosorbent assay which employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al, published by Lange Medical Publications of Los Altos, Calif., in 1982, which is incorporated herein by reference.

"EMIT" refers to an enzyme-multiplied immunoassay technique which uses (1) an enzyme-labeled hapten, (2) specific antibody to the hapten, (3) pretreatment reagent, (4) buffered-enzyme substrate, and (5) standards to detect the amount of an unknown in a sample. A description of the EMIT technique is found in *Enzyme Immunoassay*, edited by E. T. Maggio, published in 1980 by CRC Press, Inc., Boca Raton, Florida, particularly on pp. 141-150, 234-5, and 242-3. These materials are incorporated by reference.

"Epitope" refers to that portion of a molecule which is specifically recognized by an antibody. It is also referred to as a determinant.

"Fluoroimmunoassay" refers to an antibody-based assay in which the species to be measured binds to, displaces or competes for binding with a material labelled with a fluorescent species in an antibody-ligand complex. In some embodiments of this assay, the complex is separated and the presence or absence of fluorescent species gives a measure of the amount of measured species. In other embodiments, the complex has different fluorescent properties than the uncomplexed fluorescent species so that the formation of the complex can be detected without separation of the complex. A description of fluoroimmunoassay techniques is found in "A Review of Fluoroimmunoassay and Immunofluorometric Assay", D. S. Smith et al. (1981) *Ann. Clin. Biochem.* (1981) 18:253-274 which is incorporated herein by reference.

"Hapten" refers to a compound, usually of low molecular weight, which when bound to a larger molecule can give rise to antibody formation.

"Influenza" refers to a disease state brought about by infection by an influenza virus. Among the influenza viruses are Type A and Type B viruses. These Type A and B are recognized in the field. A number of these have been identified and are present in and available from the American Type Culture Collection. These representative materials are described at pages 272-276 in "American Type Culture Collection Catalogue of Strains II, Fourth Edition" (1983), R. Hay, et al, Eds, American Type Culture Collection, Rockville, Md., which is incorporated herein by reference.

"Label" refers to a detectable group in a molecule. Among the common labels are radioactive species useful in radioimmunoassays, fluorescent species useful in fluoroimmunoassays, and enzymatic species useful in the ELISA and EMIT methods and the like.

"Ligand" refers to any molecule which has an antibody combining site and can bind to a receptor.

"Lower alkyl" refers to a straight or branched chain saturated hydrocarbon group having from 1 to 4 carbon atoms such as, for example, methyl, ethyl, n-propyl, isopropyl, n-butyl, isobutyl, sec-butyl, and tertbutyl.

"Matrix protein" or "M protein" refer to a protein constituent of influenza and related viruses. It is described in detail herein in the Background section.

"Peptide" or "polypeptide" refers to relatively low molecular weight compounds which yield two or more amino acids on hydrolysis.

"Pharmaceutically acceptable salt" and "salt" refer to salts that retain the desired antigenic activity of the parent polypeptide. "Pharmaceutically acceptable salt" refers to salts that are suitable for ingestion or parenteral administration or the like in that they do not impart any undesired toxicological effects. Examples of such salts and pharmaceutically acceptable salts include (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, alginic acid, polyglutamic acid, naphthalenesulfonic acids, naphthalenedisulfonic acids, polygalacturonic acid, and the like; (b) salts with monovalent and polyvalent metal cations such as sodium, potassium, zinc, calcium, barium, magnesium, aluminum, copper, cobalt, nickel, cadmium, and the like; or with an organic cation formed from N,N'-dibenzylethylenediamine or ethylenediamine; and (c) combinations of (a) and (b), e.g., a zinc tannate salt and the like.

"Radioimmunoassay" or "RIA" refers to an antibody-based assay in which the species to be measured binds to, displaces or competes for binding with a radiolabeled material in an antibody-ligand complex. The complex is separated and the presence or absence of radioactivity gives a measure of the amount of measured species.

"Receptor" refers to a region of an antibody with the capability to combine specifically with an antigen.

"Substantially corresponding" refers to the property of two amino acid sequences being identical to one another or differing from one another by no more than two amino acid units. Sequences can differ by having a different amino acid at a given position or by having an extra amino acid or by missing an amino acid. Preferably, the sequences have at most one point of difference and more preferably are identical.

"Vaccine" refers to a suspension or solution of attenuated or killed microorganisms (specifically, influenza virus) or synthetic polypeptides or conjugates administered for the prevention, amelioration or treatment of influenza via stimulation of the production of specific antibodies against the influenza virus.

As used herein, the following abbreviations are used for the amino acids described:

| | |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

These represent L-amino acids with the exception of the achiral amino acid glycine. All peptide sequences mentioned herein are written according to the generally accepted convention whereby the N-terminal (or amino-terminal) amino acid is on the left and C-terminal (carboxyl-terminal) amino acid is on the right.

Description of Preferred Embodiments

In one aspect, this invention relates to synthetic peptide sequences which have influenza antigen properties.

The synthetic sequences have about 5 to 25 and especially 15 to 25 amino acids substantially corresponding to a 15 to 25 amino acid sequence of the 215-239 region, and preferably from 15 to 22 amino acids substantially corresponding to a 15 to 22 amino acid sequence of the 215-236 region of the type A influenza virus matrix protein. The 215-239 region of the matrix protein has the sequence

```
215                   220                    225
Met—Ala—Arg—Thr—Ile—Gly—Thr—His—Pro—Ser—Ser—Ser—
              230                    235
Ala—Gly—Leu—Lys—Asn—Asp—Leu—Leu—Glu—Asn—Leu—Gln—Ala
```

In preferred embodiments, the synthetic sequence is from 15 to 20 amino acids in length and includes the 231 region. More preferably, it is 17-18 amino acids in length and substantially corresponds to the 220-236 region. An especially preferred embodiment has the amino acid sequence:
H—Gly—Thr—His—Pro—Ser—Ser—Ser—Ala—
  Gly—Leu—Lys—Asn—Asp—Leu—Leu—
  Glu—Asn—OH The preparation of these synthetic polypeptides will be set forth below in the General Preparative Techniques section.

The present invention also contemplates salts of any of these polypeptides—especially pharmaceutically acceptable salts—the polypeptides wherein the amino-terminal amino acid is blocked using an acyl group (particularly an acetyl group) and/or wherein the carboxy-terminal amino acid has been converted to an amide group. The preparation of typical salts and blocked materials will be set forth below in the General Preparative Techniques section.

In the aspect of the invention wherein the polypeptides are conjugated with a macromolecular carrier, suitable carriers are typically large, slowly metabolized macromolecules such as proteins; polysaccharides, such as latex functionalized sepharose, agarose, cellulose beads and the like; polymeric amino acids, such as polyglutamic acid, polylysine and the like; and amino acid copolymers. Especially useful protein substrates are serum albumins, keyhole limpet hemocyanin, immunoglobulin molecules, thyroglobulin, ovalbumin, and other proteins well known to those skilled in the art.

Such protein carriers may be used in their native form or their functional group content may be modified by succinylation of Lys residues or reaction with Cys-thiolactone. A sulfhydryl group may also be incorporated into the carrier (or the synthetic polypeptide) by reaction of amino functions with 2-iminothiolane or the N-hydroxysuccinimide ester of 3-(4-dithiopyridyl) proprionate. Suitable carriers may also have been modified to incorporate spacer arms (such as hexamethylene diamine or other bifunctional molecules of similar size) for attachment of the synthetic peptides. The conjugating species may also incorporate labels, if desired. As in the case of the polypeptides themselves, these conjugates can have either or both of their terminal amino acids converted to acyls or amides, as appropriate. The preparation of such conjugates will be set forth below.

The peptides of this invention and particularly their conjugates exhibit influenza antigenic properties. Accordingly, they can be used in assay techniques where this property can be utilized.

The influenza antigenic properties of the peptides and their conjugates also can come into play in therapeutics. In one such application, the peptide or conjugate is used to produce antibodies specific to influenza. In the process, a host animal is challenged with the polypeptide or conjugate to elicit the production of the antibody which is then collected. This process is set forth in detail in the General Preparative Techniques section. In another application the peptide or its pharmaceutically acceptable salt is used to suppress transcriptase activity.

General Preparative Techniques

Chemical Synthesis of the Polypeptide Sequence

The polypeptides may be synthesized by any techniques that are known to those skilled in the peptide art, such as may be found in Meienhofer, J. *Hormonal Proteins and Peptides*, Vol. 2, p. 46, Academic Press, New York, (1973) (for solid phase peptide synthesis) and Schroder, E. et al. *The Peptides*, Vol. 1, Academic Press, New York, (1965) (for classical solution synthesis).

These methods comprise sequential addition of amino acids or suitably protected amino acids to a growing peptide chain. Generally, either the amino or carboxyl group of the first amino acid is protected by a suitable protecting group. The protected or derivatized amino acid is contacted with the next amino acid in the sequence having the complimentary (amino or carboxyl) group suitably protected, under conditions suitable for forming the amide linkage. The protecting group is then removed from this newly added amino acid residue and the next amino acid is then added. After all the desired amino acids have been linked in the proper sequence, any remaining protecting groups (and any solid support) are removed sequentially or concurrently to afford the final polypeptide. Also, as is well known, it is possible to add more than one amino acid at a time to a growing chain.

A preferred method of preparing compounds of the present invention involves solid phase peptide synthesis. In this method the alpha-amino function of the amino acids is protected by an acid or base-sensitive group. Suitable protecting groups are t-butyloxycarbonyl (Boc), fluorenyl methyloxy carbonyl (FMCC), benzyloxycarbonyl (Z), and the like.

Side chain active sites are protected, as well, to prevent undesired reactions or couplings. Particularly preferred side chain protecting groups are, for arginine: nitro, p-toluenesulfonyl, 4-methoxybenzenesulfonyl, Z, Boc, and adamantyloxy carbonyl; for lysine: dichloro benzyloxyl carbonyl, t-Boc; for Asp and Glu: o-benzyl, t-butyl; for tyrosine: benzyl, o-bromobenzyloxycarbonyl, 2,6-dichlorobenzyl, isopropyl, cyclohexyl, cyclo pentyl, and acetyl; for serine and threonine: benzyl, t-butyl and tetrahydro pyranyl; for histidine: benzyl, p-toluenesulfonyl and 2,4-dinitrophenyl; and for Trp: formyl.

The carboxyl-terminal amino acid is attached to a suitable solid support. Suitable supports are inert to the reagents and reaction conditions of the reactions, as well as insoluble in the media used. Suitable solid supports include chloromethylpolystyrenedivinylbenzene polymers and the like, especially chloromethylpolystyrene-1% divinylbenzene polymer. For the special case where the carboxy-terminal amino acid of the peptide becomes an amide [—C(=O)—NH$_2$], a particularly useful support is the benzhydrylamino-polystyrene-divinylbenzene polymer described by Vivaille, P. et al. (1971) $Helv. Chim. Acta.$ 54:2772. The attachment to the chloro-methyl polystyrene-divinylbenzene type of resin is made by means of the reaction of the alpha N-protected amino acid, especially the Boc-amino acid, as its cesium, tetramethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resins at an elevated temperature, for example between about 40° C. and 60° C., preferably about 50° C., for from about 12 to 48 hours, preferably about 24 hours. The alpha N-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° C. and 50° C., preferably 25° C. in a solvent such as dichloromethane or DMF, preferably dichloromethane.

The removal of the alpha N-protecting groups may be performed in the presence of, for example, a solution of trifluoroacetic acid in methylene chloride, or other strong acid solution, preferably 50% trifluoroacetic acid in dichloromethane at about ambient temperature. Base-labile protecting groups may be removed by treatment with a base such as piperidine in DMF. Each protected amino acid is preferably introduced in approximately 2.5 molar excess and coupling may be carried out in dichloromethane and the like, especially in methylene chloride at about ambient temperature. The coupling agent is normally DCC in dichloromethane but may be N,N'-diisopropylcarbodiimide or other carbodiimide either alone or in the presence of HBT, N-hydroxysuccinimide, other N-hydroxyimides or oximes. Alternatively, protected amino acid active esters (e.g., p-nitrophenyl, pentafluorophenyl and the like) or symmetrical anhydrides may be used.

At the end of the solid phase synthesis, the polypeptide is either carried through another deprotection and neutralization cycle followed by acylation, preferably acetylation with acetic anhydride to yield an N-acetyl (N-Ac) blocked amino end group, or it may be removed from the resin directly. If the carboxy.[—C(=O)—OH] terminal is to be blocked as the amide, the peptide may be either synthesized on the benzhydrylamino-polystyrene resin, which gives the amide directly, or it may be removed from the resin by ammonolysis with, for example, ammonia/methanol or ammonia/ethanol, at a temperature of from about 0° to about 50° C., preferably about 25° C. for about 12 to about 48 hours, preferably about 18 hours. If a peptide with a free amino-terminal and a carboxyl-terminal is desired, the peptide may be directly removed from the resin by treatment with anhydrous liquid hydrogen fluoride in the presence of a radical scavenger such as anisole. The amino or carboxyl-blocked (protected) peptides, either on the resin or removed from the resin by ammonolysis, are similarly deprotected by treatment with anhydrous liquid hydrogen fluoride. In cases where base-labile protection of the alpha N function is used in conjunction with t-butyl-based side chain protection, the final resin removal and deprotection step may be performed with trifluoroacetic acid.

Other means of removal of the (side chain) protecting groups from the polypeptide are treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia or with liquid hydrogen fluoride plus anisole at a temperature between about $-10°$ and $+10°$ C., preferably about 0° C., for between about 15 minutes and 1 hour, preferably about 30 minutes. The latter treatment (HF/anisole) may be used for simultaneous cleavage from the resin and deprotection to yield free—CO$_2$H end groups when a normal benzylester linkage has been used or to form a CO—NH$_2$ (amide) end groups when a benzhydrylamino linkage has been used. For the amide terminal peptides on the benzhydrylamine resins, the resin cleavage and deprotection steps may be combined in a single step utilizing liquid HF/anisole as described above. The fully protected polypeptide can then be purified by chromatographic steps.

Salt Formation

The peptides can be obtained as salts, by simple adjustment of the pH of the medium from which they are finally recovered with acids or bases corresponding to the desired counter ions.

Conjugation to Carriers

The polypeptides described herein can be coupled to carriers through several types of functional groups on the polypeptides. These include (a) alpha or epsilon-amino groups, (b) alpha, beta or gamma-carboxyl groups, (c) thiol groups, and (d) aromatic rings in the peptides.

Alpha and epsilon-amino groups can be coupled by several methods. In one they are reacted with activated carboxyl groups in the carrier. This activation can be carried out with carbodiimides, especially water soluble carbodiimides (WSC) such as N-ethyl-N'-(3-dimethylaminopropylcarbodiimide), isoxazolium salts, 1- ethoxycarbonyl-2-ethoxy1,2-dihydroquinoline, active ester forming reagents (to yield N-hydroxysuccinimide esters, 1-hydroxybenzotriazole esters, nitrophenyl esters, pentafluorophenyl esters, etc.), reagents yielding acid chlorides (e.g., $PCl_5$, but only for nonprotein carriers), reagents yielding mixed anhydrides (e.g., acetic anhydride) and the like.

The free amino function of the synthetic peptide (either the alpha-amino function or an epsilon-amino function of lysine) is then reacted with the activated carboxyl function of the carrier in an aqueous buffer or in a mixed organic/aqueous buffer system (e.g., DMF/water), pH 8). For nonprotein carriers, an organic solvent (e.g., DMF) may be used. Especially useful techniques in this class are concurrent activation of a protein carrier with and coupling with peptide in aqueous buffer or preparation of the p-$NO_2$-phenyl ester of a succinylated protein carrier followed by coupling with the peptides in aqueous buffer.

In another method, the amino function(s) on the synthetic peptide may be cross-linked with amino functions on the carrier molecule by reaction with glutaraldehyde in aqueous solution on mixed organic/aqueous solution (pH of about 7) at room temperature, or by reaction with bifunctional cross-linking reagents such as dimethylsuberimidate, phenyldiisocyanate, phenyldiisothiocyanate, difluorodinitrobenzene, or cyanic chloride.

Alpha, beta or gamma-carboxyl groups on the peptides can be reacted with amines on the carrier in the converse of the above process. The carboxyl functions on the synthetic peptide will be activated by the techniques just recited. The activated carboxyl functions will then be reacted with the amino functions on a suitable carrier molecule using the aqueous or mixed organic/aqueous buffer conditions described above.

Thiol (—SH) groups present on the synthetic polypeptide chain can be reacted with carriers which have been modified by the incorporation of maleimide functions. The -SH function inserts specifically into the double bond of the maleimide function and yields a peptide-carrier complex. The SH function may be incorporated into the peptide by reaction of an amino function (alpha-amino or epsilon-amino of lysine) with cysteine thiolacetone.

Aromatic rings present in the peptides' Tyr and His units may be cross-linked to the aromatic rings of Tyr and His residues of protein carrier by means of bisdiazotized aromatic compounds (e.g., bis-diazotized benzidine or bis-diazotized o-anisidide). This reaction is performed on an aqueous or mixed organic/aqueous solution of the antigen and carrier. For a review of such techniques, see B. F. Erlanger in *Methods of Enzymology* (1980), 70:85, "The Preparation of Antigenic Hapten-Carrier Conjugates—A Survey".

Preparing Labeled Versions of the Peptides

Radiolabeled versions of the polypeptides can be produced in several manners. For one, commercially available $^{14}$carbon-labeled amino acids can be employed in the synthesis of the polypeptides. Similarly $^3$H-amino acids can be prepared by the magnesium oxide procedure of Schwyzer et al. (1959) *Helv. Clin. Acta*, 42 2622. Except for the precautions routinely associated with radiochemicals, these processes can follow the usual synthesis route. Alternatively, the finished polypeptide or conjugate can be radiolabeled by tritium exchange.

Enzyme labels can be incorporated by using an enzymic carrier for forming conjugates or by attaching an enzymatically active group to the carrier or the peptide Generation of Antibodies to the Synthetic Peptides Methods for generating antibodies to antigens using host animals are known generally to the art. In a typical preparation, one or more of the synthetic polypeptide sequences is introduced into a mammalian or avian host. Suitable hosts include, for example, monkeys, cattle, rabbits, rats, mice, and the like. This is usually accomplished by subcutaneous injection as a solution in saline which has been emulsified with complete Freund's adjuvant.

The antibodies are collected by bleeding the animal after about a month. The whole blood is allowed to clot at 25° C. for several hours. Aqueous ammonium sulfate solution is added to achieve 40% by weight of aqueous solution, and the IgG fraction precipitates. The precipitate is collected by centrifugation and resuspended in saline or buffer solution to the desired concentration.

The purified antibody fraction may be further modified for use in diagnostic assay systems. Such modification may encompass linkage with enzymes such as lipozyme, lactoperoxidase, alkaline phosphatase and others for use in ELISA assays. The antibody may be modified with fluorescent moieties. Optimally, this fluorescence may be quenched or enhanced upon binding of the antibody and antigen. These techniques for assaying the extent of the antibody-antigen interaction are known in the art. An essential first step is, however, the preparation a suitably immunogenic synthetic influenza polypeptide for administration to the animals so that a population of high affinity antibodies will be obtained.

The Transcriptase Assay (and Inhibition)

The conditions for the transcriptase assay will be according to those described by Kato and associates for the ApG-primed RNA polymerase assay. (Reference on page 6) Purified M protein is added at varying concentrations and states of dispersion to determine optimal conditions for attainment of maximal suppression. The use of monoclonal antibodies to defined antigenic sites to reverse inhibition assists in localizing the segment of M-protein responsible for inhibition. Synthetic peptides are assayed for their ability to suppress transcriptase activity.

Utility and Administration

In the practice of the medical and veterinary methods of this invention an effective amount of a polypeptide or conjugate or antibody thereto of this invention or a pharmaceutical composition containing the same is administered to the subject in need of such treatment. These polypeptides, conjugates or antibodies or compositions may be administered by any of a variety of routes depending upon the specific end use, including particularly parenterally (including subcutaneous, intramuscular, and intravenous administration). Oral administration can also be used, particularly with stable forms of these materials. The most suitable route in any given case will depend upon the use, particular active ingredient, the subject involved, and judgment of the medical or veterinary practitioner.

The materials can be administered to mammals such as man, monkeys, dogs, rodents, and the like, and to nonmammalian species such as avian, for example, domestic fowl, including turkeys, chickens, ducks, and the like.

In such uses, the compositions generally include a pharmaceutical diluent such as injectable saline, mineral oil or the like. For oral administration, tablets, including enteric-coated tablets, may be used, and in the case of veterinary applications, oral administration can be effected using treated feeds. The compound or composition may also be administered by means of slow-release, depot, or implant formulations, as is well known in the art. The polypeptides, polypeptide conjugates and antibodies described herein are usually administered in amounts of 1 to 1000 micrograms per kg of body weight, particularly in amounts of 5–600 micrograms per kg of body weight.

For active immunity, the polypeptide or the polypeptide conjugate is administered to produce influenza antibodies in the subject in need of treatment. In passive immunity, partially purified serum containing antibodies from host animals is introduced into the subject to produce a therapeutic effect.

It has also been observed that M-protein can have an inhibiting effect on the activity of polymerase of influenza virus as well as on the transcriptase activity in influenza virus. This suggests that M-protein can modulate and suppress viral replication. (Ye. Z. et al. (1987) *J. Virol.* 61:239–246; Zvonarjev, A. Y. et al. (1980)*J. Virol.* 33:583–586.) It has further been noted that monoclonal antibodies directed to specific sites on the M-protein can reduce or reverse this activity of the M-protein. The present synthetic peptides correspond to such a specific site and as conjugates exhibit a very high titer against certain monoclonal antibodies. As such, it would be expected that the peptides and their conjugates would inhibit viral replication, in the manner of M-protein, and thus function as an antiviral component.

The polypeptides, polypeptide conjugates and antibodies to these polypeptides and polypeptide conjugates of this invention are also useful in the detection and diagnosis of influenza, particularly in providing high purity materials useful for calibration solutions for assay techniques, such as ELISA or EMIT.

The enzymes for use in the diagnostic reagents, standards or kits can vary widely, depending on the ease of conjugation, turnover rate, and the physiological fluid in which the unknown (analyte) is to be measured. Representative enzymes of choice include hydrolysases, nucleases, amidases, esterases and the like which are found in U.S. Pat. No. 3,817,837, which is incorporated herein by reference.

The methods and apparatus for labeling an antibody as described herein for use in a diagnostic reagent, standard or kit is found in U.S. Pat. No. 4,366,241, which is incorporated herein by reference.

EXAMPLES

The following examples serve to illustrate the invention. The should not be construed as narrowing it, or limiting its scope.

EXAMPLE 1

Preparation of H—Gly—Thr—His—Pro—Ser—Ser—Ser—Ala—Gly—Leu—Lys—Asn—Asp—Leu—Leu—Glu—Asn—OH This peptide is synthesized by solid-phase techniques on a Beckman Model 990C peptide synthesizer using commercially available t-Boc amino acid polystyrene resin and t-Boc protected amino acids with the following side-chain protecting groups: 0-benzyl esters for Asp and Glu; 0-benzyl ethers for Thr and Ser; dnp for His; and orthochlorobenzyloxycarbonyl for Lys. All couplings are performed using a 3-molar excess of t-Boc amino acid and dicyclohexyl carbodiimide (DCC) over the number of milliequivalents of amino acid on the resin. In the case of Asn and Gln, a 3-molar excess of the t-Boc amino acid, DCC, and N-hydroxybenzotriazole (HOBT) are used. All couplings are monitored by the ninhydrin test (Kaiser, et al. *Anal Biochem* 34:595 (1970).) Forty percent TFA-$CH_2Cl_2$ is used for Boc deprotection. 2-Mercaptoethanol (0.1%) is added to the TFA/$CH_2Cl_2$ when methionine is present. (Methionine is used with an unprotected sulfhydryl side chain.) The details of the synthetic cycle are given in Schedule 1.

Schedule 1

SCHEDULE OF EVENTS FOR ASSEMBLING THE PEPTIDE ON RESIN

| Step | Reagent or Solvent | | Time (min) |
|---|---|---|---|
| 1 | $CH_2Cl_2$ | 3 times | 1.5 |
| 2 | 40% TFA/$CH_2CL_2$ prewash | | 5 |
| 3 | 40% TFA/$CH_2Cl_2$ | | 30 |
| 4 | $CH_2Cl_2$ | 6 times | 1.5 |
| 5 | 80% Isopropanol/$CH_2Cl_2$ | 3 times | 1.5 |
| 6 | $CH_2Cl_2$ | 3 times | 1.5 |
| 7 | 5% Diisopropylethylamine/ $CH_2Cl_2$ | 2 times | 10 |
| 8 | $CH_2Cl_2$ | 3 times | 1.5 |
| 9 | Coupling: 3-fold excess of t-Boc amino acid in $CH_2Cl_2$: DMF(2:1, v/v); DCC/$CH_2Cl_2$ | | 120 |
| 10 | $CH_2Cl_2$ | 3 times | 1.5 |
| 11 | 80% Isopropanol/$CH_2Cl_2$ | 3 times | 1.5 |

After completion of the synthesis, the peptide is cleaved from the resin using a low-high HF procedure (see Tam et al, (1982) *Tett. Lett.*, 23, 2939, and *J. Am. Chem. Soc.*, (1983) 105, 6442), and $S_N2$ deprotection reaction in HF-reaction Apparatus Type II (Peninsula Labs). The peptide resin is first treated with an HF:dimethylsulfide:p-cresol mixture (25:65:10) at 4° C. for 1 hr. HF and dimethyl-sulfide are evaporated completely. Next, more HF is distilled into the reaction vessel to make the ratio of HF-p-cresol 9:1. The mixture is stirred at 4° C. for 45 min. After that, HF is evaporated completely, first at 4° C. and then at room temperature, under vacuum. At low HF concentration, Asp and Glu side-chain benzyl ester groups are cleaved, with minimum acylation side reactions. The high-HF step removes more acid-stable groups such as Arg (Tos) and cleaves the peptide from the resin completely. The DNP group of His is removed before HF cleavage by treatment with 1000-fold excess of 2-mercaptoethanol.

The peptide is separated from the various side products by extraction with ether and isolated from the resin by extraction with 5% (or higher, depending on the solubility of the peptide) acetic acid and subsequent lyophilization. The crude peptide is subjected to gel filtration on Sephadex LH-20. Final purification is achieved on HPLC using 50 cm/20 mm preparative column packed with Vydac 15-20 micron $C_{18}$. The purity of the peptide is checked by analytical HPLC and amino acid analysis.

After three lyophilizations from water, pure H—Gly—Thr—His—Pro—Ser—Ser—Ser—Ala—Gly—Leu—Lys—Asn—Asp—Leu—Leu—Glu—Asn—OH is obtained as the acetate salt In the tests which follow, this "220-236" sequence is referred to as "Peptide 1".

EXAMPLE 2

Preparation of Radiolabeled
H—Gly—Thr—His—Pro—Ser—Ser—Ser—Ala—Gly—Leu—Lys—Asn—Asp—Leu—Leu—Glu—Asn—OH The process of Example 1 is repeated using a radiolabeled Boc-amino acid prepared by the method of Schwyzer et al, Helv. Chim. Acta (1959) 42, 2622. This produces the desired radiolabeled product.

EXAMPLE 3

Preparation of Conjugates

The peptides synthesized in Examples 1 and 2 are conjugated to carrier proteins. Bovine serum albumin and thyroglobulin are used as the carriers. Conjugation is carried out using the general procedure outlined herein and the specific techniques reported by Atassi, et al., Biochem. Biophys. Acta, (1981) 670:300-302, incorporated herein by reference.

ACTIVITY TESTS

The activity of the product of Example 1 and the BSA and thyroglobulin complexes of this product is tested.

In a first test, a series of monoclonal antibodies to intact M protein are assembled and tested for reactivity with the synthetic peptide and its complexes. Balb/c mice are immunized with 10-25 micrograms to purified M-protein in Freund's complete adjuvant. The M-protein is purified by SDS gel chromatography followed by exhaustive dialysis versus distilled water from outdated swine influenza vaccine (X-53a recombinant virus strain containing A/PR/8/34 M-protein gene (Baez, N. W., et al., Virology, 107:548-551) The mice are boosted intravenously six weeks to three months later with an additional 10-25 micrograms of the M-protein. Spleens are removed three days post boost and the spleen cells are fused using polyethylene glycol glycol with SP2/0-Ag14 nonsecreting myeloma cells (ATCC CRL 1581) which are growing in log phase.

Hybridomas are selected in HAT medium and screened for reactivity by ELISA on microtiter plates coated with M-protein. Reactive hybridomas are cloned at 0.5 and 1.0 cell/well with T-cell feeder layers. Additional hybridoma lines, described by van Wyke and coworkers at *J. Virol.,* 1984, 48:248-52, and identified as 289/4 and 904/6 are furnished by their discoverers and cloned to produce 289/4-D5 and 904/6-D5. Monoclonal antibodies produced by these various hybridomas are collected.

The collection of monoclonal antibodies are first tested against a group of fourteen different purified strains of type A influenza viruses in an ELISA assay performed generally as described by Khan, et al., 1982, *J. Clin. Microbiology,* 16:813-820. In this assay microtiter plates are coated with the purified virus (100 ng/well). Following postcoating with 0.5% BSA in PBS-Tween, ascites fluids are diluted in serial three fold dilutions across the plate beginning with an initial dilution of 1:100. Sheep anti-mouse alkaline phosphatase conjugate (Sigma) is added to quantitate bound monoclonal antibody and para-nitrophenyl phosphate is employed as the substrate. End point titrations are determined as the dilution which produced an absorbance value threefold above background. The results of these tests are given in Table 1 and show that the monoclonal antibody panel has broad recognition for a wide range of influenza strains.

The three materials of the invention prepared in Examples 1 and 3 are then tested to determine their activity versus this panel of monoclonal antibodies. Results are given in Table 2 and are dramatic. They show that the peptide, when conjugated to BSA or thyroglobulin and used as an ELISA adsorbent, produces titers up to ten thousand fold greater than seen with purified M-protein for many of the monoclonal antibodies. This strong monoclonal antibody recognizing, site-specific binding of the peptides and conjugates, coupled with the knowledge that certain sites are involved in inhibiting viral replication suggest the use of the present materials as antiviral agents.

TABLE 1

INFLUENZA VIRUSES
ELISA TITERS × $10^{-3}$

| | | | H1N1 | | | | | |
|---|---|---|---|---|---|---|---|---|
| Ag. Site | Mab | M-protein | X-53a | A/PR/8/34 | A/WSN/33 | A/FM/1/47 | A/FW/1/50 | A/USSR/90/77 |
| #1A | 2BB10-G9 | 1020 | 368 | 616 | 512 | 200 | 314 | 218 |
| | 1G8-A11 | 420 | 492 | 488 | 582 | 106 | 152 | 264 |
| | 3G12-C12 | 740 | 478 | 604 | 560 | 62 | 140 | 320 |
| | 9ES-B2 | 524 | 980 | 1220 | 428 | 438 | 414 | 584 |
| | 821-BS-A8 | 306 | 126 | 212 | 346 | 134 | 126 | 118 |
| #1B | 2E5-C1 | 1500 | 1820 | 1720 | 0 | 0 | 21 | 1750 |
| | 961-G8-H3 | 468 | 326 | 474 | 4 | 1 | 24 | 332 |
| | 963-D3-G10 | 478 | 620 | 496 | 0 | 0 | 9 | 358 |
| | 6B9-B8 | 108 | 182 | 158 | 0 | 0 | 0 | 82 |
| #2 | 1G11-D11 | 540 | 750 | 1560 | 558 | 320 | 350 | 558 |
| | 951-C4-G2 | 154 | 172 | 212 | 50 | 24 | 32 | 94 |
| | 823-DS-B11 | 322 | 562 | 412 | 0 | 72 | 96 | 190 |
| | M2-1C-6** | 48 | 50 | 51 | 41 | 42 | 16 | 21 |
| | 289/4-D5* | 43 | 36 | 43 | 34 | 10 | 15 | 22 |
| #3 | 611-G10-D3 | 88 | 68 | 59 | 4 | 6 | 6 | 4 |
| | 951-D10-B3 | 70 | 46 | 96 | 4 | 1 | 8 | 2 |
| Unclassified | 611-B12-D10 | 78 | 126 | 62 | 66 | 52 | 24 | 46 |
| | 961/6-B10 | 294 | 7 | 4 | 1 | 0 | 1 | 2 |
| | 904/6-D5* | 0 | 1 | 1 | 8 | 0 | 4 | 4 |

| | H2N2 | | H3N2 | | | | | H3N8 | B |
|---|---|---|---|---|---|---|---|---|---|
| Ag. | A/Sing/ | A/Mal/ | A/Ai/ | A/Ud/ | A/PC/ | A/Tex/ | A/Ban/ | A/duck/ | B/Lee/ |

TABLE 1-continued

INFLUENZA VIRUSES
ELISA TITERS × 10⁻³

| Site | 1/57 | NY/78 | 2/68 | 307/72 | 1/73 | 1/77 | 1/79 | 1/63 | 40 |
|---|---|---|---|---|---|---|---|---|---|
| #1A | 622 | 940 | 512 | 350 | 1320 | 600 | 516 | 418 | 0 |
|  | 650 | 1360 | 642 | 290 | 980 | 608 | 398 | 392 | 0 |
|  | 640 | 1340 | 1560 | 240 | 1080 | 606 | 262 | 424 | 0 |
|  | 465 | 1380 | 1080 | 322 | 1860 | 740 | 544 | 582 | 0 |
|  | 120 | 396 | 460 | 136 | 450 | 360 | 186 | 172 | 0 |
| #1B | 0 | 0 | 0 | 0 | 0 | 0 | 0 | 0 | 0 |
|  | 3 | 5 | 20 | 1 | 7 | 5 | 2 | 2 | 0 |
|  | 0 | 0 | 1 | 0 | 0 | 0 | 0 | 0 | 0 |
|  | 0 | 1 | 0 | 0 | 0 | 1 | 0 | 0 | 0 |
| #2 | 590 | 1940 | 1440 | 578 | 1480 | 1480 | 340 | 598 | 0 |
|  | 330 | 418 | 194 | 94 | 214 | 219 | 91 | 106 | 0 |
|  | 654 | 960 | 560 | 582 | 580 | 560 | 196 | 272 | 0 |
|  | 80 | 90 | 70 | 40 | 58 | 84 | 24 | 34 | 0 |
|  | 62 | 78 | 71 | 62 | 56 | 64 | 24 | 41 | 0 |
| #3 | 72 | 90 | 60 | 3 | 104 | 108 | 5 | 3 | 0 |
|  | 162 | 165 | 64 | 16 | 194 | 188 | 16 | 16 | 0 |
| Unclassified | 500 | 190 | 146 | 138 | 200 | 155 | 44 | 72 | 0 |
|  | 108 | 56 | 2 | 1 | 8 | 8 | 1 | 1 | 0 |
|  | 62 | 24 | 36 | 10 | 28 | 29 | 1 | 19 | 0 |

*purified from X-53a (A/PR/8/34 M-protein gene)
**described by van Wyke and co-workers (1984) J. Virol 48:1248.

TABLE 2

Reactivity of Monoclonal Antibodies with Synthetic Peptide

| Monoclonal Antibody | ELISA Titers | | |
|---|---|---|---|
|  | Example 1 "free" | Example 3 BSA-conjugate | Example 3 thryoglobulin conjugate |
| 2BB10-G9 | <300 | <300 | <300 |
| 1G8-A11 | <300 | 370 | <300 |
| 3G12-C12 | <300 | 640 | <300 |
| 9E8-B2 | <300 | 390 | <300 |
| 821-B8-A8 | <300 | <300 | <300 |
| 2E5-C1 | 860 | 270,000 | 200,000 |
| 961-G8-H3 | <300 | <300 | <300 |
| 963-D3-G10 | <300 | 68,000 | 5,400 |
| 6B9-B8 | 1350 | 1,100,000 | 28,800 |
| 1G11-D11 | 860 | 300 | <300 |
| 951-C4-G2 | <300 | <300 | <300 |
| 823-D8-B11 | <300 | <300 | <300 |
| M2-1C6 | <300 | <300 | <300 |
| 289/4-D5 | <300 | <300 | <300 |
| 611-G10-D3 | <300 | <300 | <300 |
| 951-D10-B3 | <300 | <300 | <300 |
| 611-B12-D10 | <300 | <300 | <300 |
| 961/6-B10 | <300 | <300 | <300 |

TABLE 2-continued

Reactivity of Monoclonal Antibodies with Synthetic Peptide

| Monoclonal Antibody | ELISA Titers | | |
|---|---|---|---|
|  | Example 1 "free" | Example 3 BSA-conjugate | Example 3 thryoglobulin conjugate |
| 904/6-D5 | <300 | <300 | <300 |

What is claimed is:

1. A synthetic polypeptide exhibiting influenza virus antigenic reactivity and selected from polypeptides of from about 15 to about 22 amino acids in length and substantially corresponding to the 215-235 region of the type A influenza virus matrix protein.

2. The synthetic polypeptide of claim 1 having the amino acid sequence
H—Gly—Thr—His—Pro—Ser—Ser—Ser—Ala—Gly—Leu—Lys—Asn—Asp—Leu—Leu—Glu—Asn—OH.

3. A pharmaceutically acceptable salt of the polypeptide of claim 1.

4. The polypeptide of claim 1 further comprising a radiolabel.

5. A polypeptide of claim 1 wherein the carboxyl-terminal amino acid has been converted to a terminal amide group.

6. The polypeptide of claim 1 wherein the amino-terminal amino acid has been blocked with a terminal acyl group.

* * * * *